United States Patent [19]

Inoue et al.

[11] Patent Number: 5,912,353
[45] Date of Patent: Jun. 15, 1999

[54] PROCESS FOR PRODUCING TETRAZOLYLATED BIPHENYLMETHANE DERIVATIVES

[75] Inventors: Satoshi Inoue; Kouji Nishimura; Masaharu Yokomoto; Nobuya Sakae; Terukage Hirata, all of Takata-gun, Japan

[73] Assignee: Wakunaga Seiyaku Kabushiki Kaisha, Osaka, Japan

[21] Appl. No.: 08/973,755

[22] PCT Filed: Jun. 24, 1996

[86] PCT No.: PCT/JP96/01737

§ 371 Date: Dec. 23, 1997

§ 102(e) Date: Dec. 23, 1997

[87] PCT Pub. No.: WO97/01557

PCT Pub. Date: Jan. 16, 1997

[30] Foreign Application Priority Data

Jun. 27, 1995 [JP] Japan .................................. 7-160591

[51] Int. Cl.$^6$ .................................................. C07D 285/12
[52] U.S. Cl. .............................................................. 548/139
[58] Field of Search ............................................. 548/139

[56] References Cited

U.S. PATENT DOCUMENTS 5,654,322  8/1997  Hirata et al. .

FOREIGN PATENT DOCUMENTS

| 0 291 969 | 11/1988 | European Pat. Off. . |
| 0 656 355 | 6/1995 | European Pat. Off. . |
| 63-23868 | 1/1988 | Japan . |
| WO 94/04516 | 3/1994 | WIPO . |
| WO 95/21837 | 8/1995 | WIPO . |
| WO 96/09301 | 3/1996 | WIPO . |
| WO 96/37481 | 11/1996 | WIPO . |

OTHER PUBLICATIONS

Terukage Hirata, et al., Bioorganic and Medicinal Chemistry Letters, vol. 6, No. 13, pp. 1469 to 1474, "Acyliminothiadiazoline Derivatives: New, Highly Potent, and Orally Active Angiotensin II Receptor Antagonists", 1996.

*Primary Examiner*—Johann Richter
*Assistant Examiner*—Ebenezer Sackey
*Attorney, Agent, or Firm*—Oblon, Spivak, McClelland, Maier & Neustadt, P.C.

[57] ABSTRACT

The present invention relates to a process for producing a tetrazolylated biphenylmethane derivatives (6) or salts thereof in accordance with the below-described reaction scheme wherein $R^1$ represents an alkyl; $R^2$ represents H, etc.; Z represents a halogen, etc.; and A represents a cycloalkene, etc. According to the above process, a tetrazolylated biphenylmethane derivative can be industrially and advantageously produced with short steps.

17 Claims, No Drawings

PROCESS FOR PRODUCING TETRAZOLYLATED BIPHENYLMETHANE DERIVATIVES

This application is a 371 of PCT/JP96/01737 filed on Jun. 24, 1996.

TECHNICAL FIELD

The present invention relates to an industrially advantageous process for producing tetrazolylated biphenylmethane derivatives which have excellent angiotensin II antagonistic action and antihypertensive action and are useful as pharmaceuticals.

BACKGROUND ART

Angiotensin II is an active compound of the renin-angiotensin system, and has powerful vasopressor action and stimulating action for the synthesis and secretion of aldosterone in the adrenal cortex. It is also known to be a substance causing hypertension. Its action is considered to be caused through a specific receptor on various target organs such as adrenal cortex, kidneys, arterioles and the peripheries of sympathetic nerves. Because of such a technical background, a number of angiotensin II antagonists have been reported with a view to developing a therapeutic for hypertension.

Among them, a tetrazolylated biphenylmethane derivative on which the present inventors have previously filed an application (WO94/04516) and which is represented by the following formula (6):

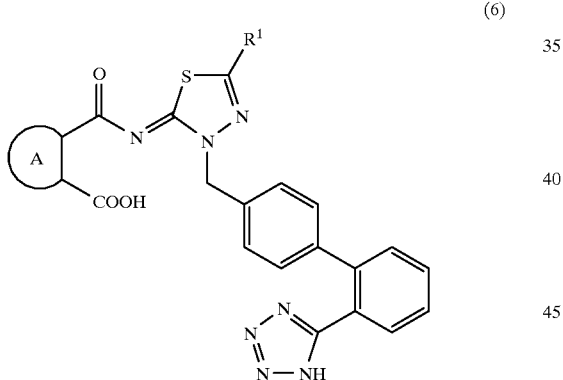

(6)

wherein $R^1$ represents a lower alkyl group and ring A represents a cycloalkane, cycloalkene or benzene ring; or a salt thereof is known to have excellent angiotensin II antagonistic action and be useful as a therapeutic for circulatory diseases such as hypertension, heart diseases and cerebral apoplexy.

As a process for producing the above biphenylmethane derivative (6), described in the international publication WO94/04516 is a process to obtain the derivative, as described in the below-described reaction scheme, by reacting a 2-(protected amino)-1,3,4-thiadiazole (7) with a protected tetrazolylated biphenylmethylbromide (8), eliminating the protecting group from the tetrazolyl group, also eliminating the amino-protecting group and then reacting with an acid anhydride (5).

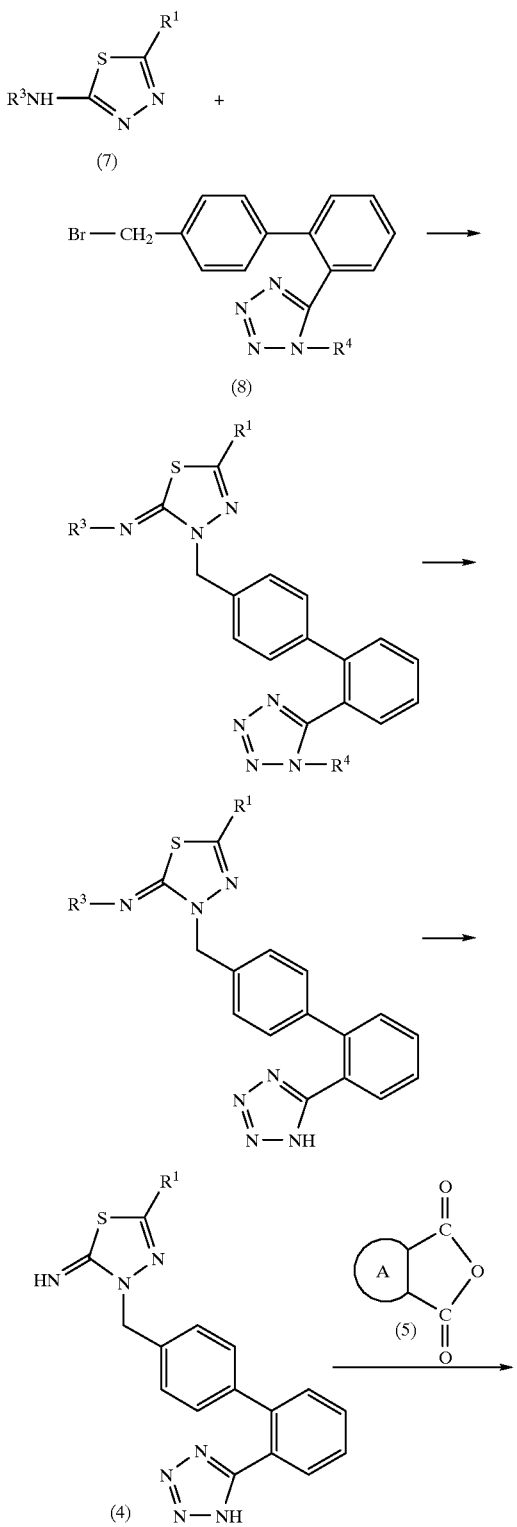

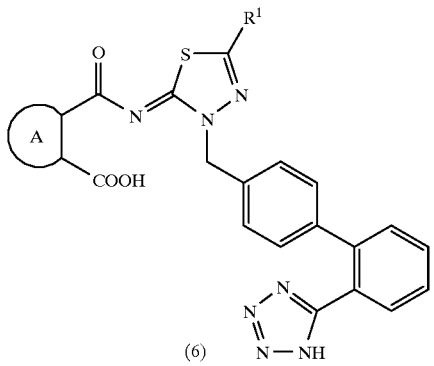

(6)

wherein $R^3$ represents an amino protecting group, $R^4$ represents a tetrazolyl protecting group (for example, triphenylmethyl group) and $R^1$ and ring A have the same meanings as defined above.

The above process is however accompanied with the drawback that the protection of a tetrazolyl group is essential so that an eliminating operation of the protecting group is required, which means increase of the steps and lowering of the yield.

Accordingly, an object of the present invention is to provide an industrially advantageous process of a tetrazolylated biphenylmethane derivatives (6) or salts thereof.

DISCLOSURE OF THE INVENTION

The present inventors therefore have carried out an extensive investigation on various production processes which do not require protection of a tetrazolyl group. As a result, it has been found that a tetrazolylated biphenylmethane derivative (6) can be obtained in a high yield without a step for the protection of a tetrazolyl group by tetrazolylation subsequent to the condensation between a cyanated biphenylmethane and a thiadiazole, leading to the completion of the present invention.

The process of the present invention is represented by the following reaction scheme.

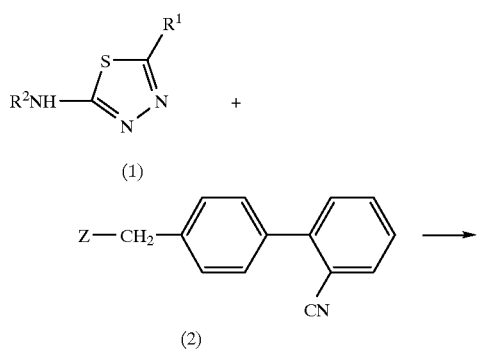

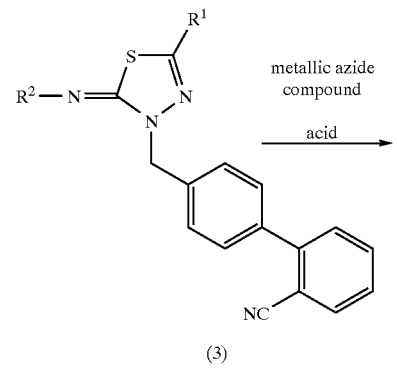

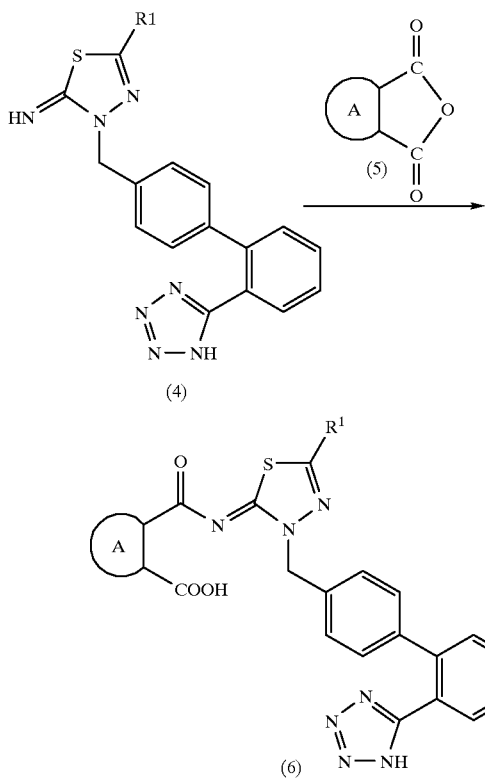

wherein $R^2$ represents a hydrogen atom or an amino-protecting group, Z represents a halogen atom or a sulfonyloxy group and $R^1$ and ring A have the same meanings as defined above.

The present invention therefore provides a process for producing a tetrazolylated biphenylmethane derivatives (6) or salts thereof, which comprises reacting a 2-(protected amino)-1,3,4-thiadiazole (1) with a cyanated biphenylmethane (2), reacting the resulting compound (3) with a metallic azide compound and an acid and, when there exists an amino protecting group, eliminating the protecting group and then reacting the resulting compound (4) with an acid anhydride (5).

BEST MODES FOR CARRYING OUT THE INVENTION

In the 2-amino-1,3,4-thiadiazole (1) used in the process of the present invention, examples of the lower alkyl group represented by $R^1$ include linear or branched alkyl groups having 1 to 7 carbon atoms, with those having 1 to 5 carbon atoms being more preferred. Specific examples of such a lower alkyl group include methyl, ethyl, n-propyl, isopropyl, n-butyl, t-butyl and n-pentyl, with an ethyl group being particularly preferred. Examples of the amino protecting group represented by $R^2$ include acyl groups such as acetyl and trifluoroacetyl groups.

In the 2-amino-1,3,4-thiadiazole (1), the amino group may be protected, but it is preferred to use an unprotected compound (an unprotected amino compound), because use of such a compound facilitates the condensation reaction with a cyanated biphenylmethane (2) and does not require an elimination step of the protecting group.

In the cyanated biphenylmethane (2), examples of the halogen atom represented by Z include chlorine, bromine and iodine atoms. Those of the sulfonyloxy group represented by Z include alkylsulfonyloxy groups such as methanesulfonyloxy, ethanesulfonyloxy and trifluoromethanesulfonyloxy and arylsulfonyloxy groups such as benzenesulfonyloxy and p-toluenesulfonyloxy.

The case of 2-amino-1,3,4-thiadiazole (1) having a protected amino group will hereinafter be explained.

A condensation reaction between a 2-(protected amino)-1,3,4-thiadiazole (1) and a cyanated biphenylmethane (2) is preferably effected in the presence of a base. Examples of the base used in the condensation reaction include sodium hydride, lithium hydride, potassium carbonate, sodium carbonate, sodium alcoholate, potassium t-butoxide, sodium hydroxide, potassium hydroxide, triethylamine and diisopropyl ethylamine. As a solvent, any solvent inert to the reaction can be used. Examples include aprotic polar solvents such as N,N-dimethylformamide and dimethylsulfoxide; ethers such as diethyl ether, tetrahydrofuran, dioxane, monoglyme and diglyme; halogenated hydrocarbons such as methylene chloride, chloroform and carbon tetrachloride; and alcohols such as methanol, ethanol and propanol.

In the condensation reaction, a phase transfer catalyst can be added as a reaction accelerator. Examples of such a phase transfer catalyst include quaternary ammonium salts such as tetramethylammonium chloride, tetraoctylammonium chloride and tetrabutylammonium bromide; pyridinium salts such as N-neopentyl-4-(N',N'-dimethylamino)-pyridinium chloride and N-(2-ethyl-hexyl)-4-(N',N'-dimethylamino) pyridinium chloride; and quaternary phosphonium salts such as tetrabutylphosphonium bromide and tetraphenylphosphonium bromide.

The condensation reaction is generally carried out at −30 to 150° C., preferably 10 to 100° C. and the reaction time is generally 10 minutes to 24 hours, preferably 1 to 10 hours.

Particularly preferred examples of the condensation reaction of the present invention include a method in which a metallic salt of a 2-(protected amino)-1,3,4-thiadiazole (1) is formed using sodium hydride or potassium carbonate as a base in an aprotic polar solvent such as N,N-dimethylformamide and then the resulting metallic salt is reacted with a cyanated biphenylmethane (2) at 0° C. to room temperature.

On the other hand, the condensation reaction between a 2-amino-1,3,4-thiadiazole (unprotected amino compound) (1) and a cyanated biphenylmethane (2) may be carried out in a suitable solvent at 20 to 200° C. for 1 to 50 hours. Any solvent can be used here insofar as it is inert to the reaction. Examples include aprotic polar solvents such as N,N-dimethylformamide, dimethylsufoxide and acetonitrile; ethers such as diethyl ether, tetrahydrofuran, dioxane, monoglyme and diglyme; halogenated hydrocarbons such as methylene chloride, chloroform and carbon tetrachloride; alcohols such as methanol, ethanol and propanol; and water. These solvents can be used either singly or in combination as needed.

The compound (3) so obtained is tetrazolylated by reacting the compound (3) with a metallic azide compound and an acid. Examples of the metallic azide usable here include tri($C_{1-18}$ alkyl)tin azide, tri($C_{1-18}$ alkyl)silyl azide and sodium azide, while those of the acid include mineral acids such as hydrochloric acid and sulfuric acid and Lewis acids such as zinc chloride and aluminum chloride.

The tetrazolylating reaction is carried out, for example, by adding a metallic azide compound to the compound (3) in a solvent such as benzene or toluene, reacting them under heat and then treating the reaction mixture with hydrochloric acid or the like. Alternatively, the tetrazolylating reaction is carried out by adding sodium azide and a Lewis acid to the compound (3) in a solvent such as butanol and then reacting them under heat.

When the compound (3) has an amino-protecting group, the protecting group should be eliminated after the tetrazolylating reaction. For the deprotection, any known reaction can be used. For example, deprotection is carried out in an aqueous alkaline solution such as an aqueous sodium hydroxide solution, an aqueous potassium hydroxide solution or an aqueous sodium carbonate solution or an acid solution such as hydrochloric acid or acetic acid in a solvent miscible with water such as ethanol, methanol, tetrahydrofuran or N,N-dimethylformamide or in a solventless manner at room temperature to 100° C.

The ring A in the acid anhydride (5) used in the reaction with the compound (4) is a cycloalkane, cycloalkene or benzene ring. Examples of the cycloalkane include cycloalkanes having 3 to 7 carbon atoms, more specifically, cyclopropane, cyclobutane, cyclopentane, cyclohexane and cycloheptane. Examples of the cycloalkene include cycloalkenes having 3 to 7 carbon atoms, more specifically, cyclopropene, cyclobutene, cyclopentene, cyclohexene and cycloheptene. Among them, a cycloalkene is more preferred, with a cyclopentene being particularly preferred.

The reaction between the compound (4) and the acid anhydride (5) can be carried out at −70 to 100° C. in an aprotic polar solvent, for example, a halogenated hydrocarbon such as methylene chloride, chloroform, carbon tetrachloride or chlorobenzene; an aromatic hydrocarbon such as benzene or toluene; an ether such as tetrahydrofuran or dioxane; or acetonitrile or N,N-dimethylformamide in the presence or absence of a base such as pyridine, picoline, N,N-dimethylaniline, N-methylmorpholine, dimethylamine, triethylamine, sodium carbonate or potassium carbonate at 0° C. to room temperature.

The target compound (6) thus obtained can be converted into a pharmaceutically acceptable salts thereof in a manner known to date. Examples of the salt include alkali metal salts such as sodium salts and potassium salts and alkaline earth metal salts, with monopotassium salts and dipotassium salts being particularly preferred.

To obtain a potassium salt of the compound (6), it is only necessary to dissolve the compound (6) in a potassium hydroxide solution, followed by precipitation as a salt. The potassium hydroxide solution to be used here is preferably a solution obtained by dissolving potassium hydroxide, in an amount at least one equivalent to the compound (6), in water, methanol, ethanol, n-propyl alcohol, isopropyl alcohol or acetone. The temperature at which the compound (6) is dissolved in the potassium hydroxide solution may be determined as desired between room temperature and a temperature higher enough to complete the dissolution under heat depending on the compound (6). In addition, a salt precipitation method can be chosen as desired, because some salts precipitate when simply left over but some salts do not precipitate until the solvent is removed to some extent.

A mono- or di-potassium salt of the compound (6) so obtained can be purified in a manner known to date, for example, by dissolving it in one or more solvents selected from water, methanol, ethanol, n-propyl alcohol, isopropyl alcohol and acetone, followed by recrystallization.

The target compound (6) or salts thereof according to the present invention has excellent angiotensin II antagonistic action and antihypertensive action and is useful as a therapeutic for circulatory diseases.

EXAMPLES

The present invention will hereinafter be described more specifically by examples but it should however be borne in mind that the present invention will not be limited to or by the following examples.

Referential Example 1

Synthesis of 2-amino-5-ethyl-1,3,4-thiadiazole

To a mixture of 1.0 kg of thiosemicarbazide and 0.9 kg of propionic acid was added dropwise 2.0 liters of concentrated sulfuric acid on ice, followed by stirring at 100° C. for 4 hours. After cooling, the reaction mixture was poured into 10 liters of ice water, and the resulting mixture was made alkaline with a 28% aqueous ammonium solution. Powders so precipitated were collected by filtration, washed successively with water, acetone and diethyl ether and dried, whereby 1.2 kg of the title compound were obtained.

Melting point: 200–203° C.
$^1$H-NMR (DMSO-$d_6$): 1.21 (3H, t, J=8 Hz), 2.80 (2H, q, J=8 Hz), 6.99 (2H, br).

Referential Example 2

Synthesis of 2-trifluoroacetamido-5-ethyl-1,3,4-thiadiazole

To a suspension of 200 g of 2-amino-5-ethyl-1,3,4-thiadiazole in 3 liters of toluene, was added 260 ml of triethylamine at room temperature. To the mixture was added dropwise 265 ml of trifluoroacetic anhydride on ice, followed by stirring at room temperature for one hour. Water was added to the reaction mixture, and the crystals so precipitated were collected by filtration. Ethyl acetate was added to the filtrate. The organic layer was dried over anhydrous magnesium sulfate, and the solvent was removed under reduced pressure, whereby 237.5 g of the title compound was obtained.

$^1$H-NMR (CDCl$_3$): 1.44 (3H, t, J=8 Hz), 3.09 (2H, q, J=8 Hz)

Referential Example 3

Synthesis of 4'-bromomethyl-2-cyanobiphenyl

To 110 ml of carbon tetrachloride, were added 10.5 g of 4'-methyl-2-cyanobiphenyl, 9.79 g of N-bromosuccinimide and 120 mg of 2,2'-azodiisobutylonitrile, followed by heating under reflux for 2 hours. After hot filtration of the insoluble matter, the filtrate was allowed to cool to room temperature. Crystals so precipitated were collected by filtration, whereby 6.6 g of the title compound was obtained.

$^1$H-NMR (CDCl$_3$): 4.56 (2H, s), 7.42–7.67 (3H, m), 7.52 (4H, s), 7.78 (1H, d, J=7 Hz).

Example 1

Synthesis of 2-trifluoroacetylimino-5-ethyl-3-(2'-cyanobiphenyl-4-yl)methyl-1,3,4-thiadiazoline (1) To a suspension of 124.1 g of sodium hydride (55% dispersion in oil) in 1.5 liters of N,N-dimethylformamide was added 533.7 g of 2-trifluoroacetamido-5-ethyl-1,3,4-thiadiazole on ice. After the evolution of hydrogen subsided, a solution of 643.6 g of 4'-bromomethyl-2-cyanobiphenyl in 3 liters of N,N-dimethylformamide was added dropwise. The resulting mixture was stirred at room temperature for one hour and then at 80° C. for 5 hours, followed by concentration under reduced pressure. Water and ethyl acetate were added to the concentrate. The organic layer was then washed with water, dried over anhydrous magnesium sulfate and concentrated under reduced pressure. The residue was subjected to column chromatography on silica gel and eluted with a 3:1 mixture of hexane and ethyl acetate. Crude crystals were recrystallized from ethanol, whereby 490.8 g of the title compound was obtained.

Appearance: Colorless prism crystals
Melting point: 106–107° C.
$^1$H-NMR (CDCl$_3$): 1.39 (3H, t, J=8 Hz), 3.95 (2H, q, J=8 Hz), 5.60 (2H, s), 7.43–7.79 (8H, m).

(2) To 18 liters of N,N-dimethylformamide, 2.44 kg of 2-trifluoroacetamido-5-ethyl-1,3,4-thiadiazole and 2.80 kg of 4'-bromomethyl-2-cyanobiphenyl were added, followed by the addition of 894 g of anhydrous potassium carbonate and 60 g of potassium iodide. The resulting mixture was stirred at room temperature for 41 hours. The insoluble matter was filtered off and the filtrate was concentrated under reduced pressure. To the concentrate, 45 liters of water and 18 liters of ethyl acetate were added to separate an organic layer. The resulting organic layer was dried over anhydrous magnesium sulfate and concentrated under reduced pressure. When the organic layer was concentrated to half of its initial volume, the precipitated crystals were collected by filtration and washed successively with ethanol and isopropyl ether. The crystals so obtained were recrystallized from 5 liters of ethanol, whereby 2.70 kg of crystals was obtained. The crystals were subjected to column chromatography on silica gel (silica gel: 10 kg, eluent: n-hexane:acetic acid=3:1→2:1), whereby 2.64 kg of the title compound was obtained. All the filtrates were combined, and the solvent was removed under reduced pressure. To the residue, 3 liters of ethanol was added, followed by hot dissolution. To the resulting solution, 300 g of activated charcoal was added and the resulting mixture was stirred under heat at 80° C. for 30 minutes. The reaction mixture was filtered through Celite. The filtrate was allowed to stand overnight at room temperature and crystals so precipitated were collected by filtration. The crystals so obtained were treated again with activated charcoal, whereby 562 g (purity: 98%) of the target compound was obtained. The filtrate was distilled off and the residue was subjected to column chromatography (silica gel: 4 kg, eluent: n-hexane:ethyl acetate= 5:1) so that 371 g of the title compound was obtained. In total, 3.57 kg of the title compound was obtained.

Appearance: Colorless prism crystals
Melting point: 106–107° C.
$^1$H-NMR (CDCl$_3$): 1.39 (3H, t), 2.95 (2H, q), 5.60 (2H, s), 7.43–7.79 (8H, m).

Example 2

Synthesis of 5-ethyl-2-imino-3-(2'-cyanobiphenyl-4-yl)methyl-1,3,4-thiadiazoline.hydrobromide (1) To 10 ml of methanol, 2.7 g of 2-amino-5-ethyl-1,3, 4-thiadiazoline and 1.3 g of 4'-bromomethyl-2- cyanobiphenyl were added, followed by heating under reflux for 20 hours. After the reaction mixture was cooled, crystals so precipitated were collected by filtration. The resulting crystals were washed successively with methanol and diethyl ether and then dried, whereby 2.12 g of the title compound was obtained.

Melting point: 225–228° C.

$^1$H-NMR (DMSO-$d_6$): 1.24 (3H, t, J=7 Hz), 2.93 (2H, q, J=7 Hz), 5.52 (2H, s), 7.49–7.99 (8H, m), 10.12 (2H, brs).

(2) To 10 ml of ethanol, 2.7 g of 2-amino-5-ethyl-1,3,4-thiadiazole and 1.3 g of 4'-bromomethyl-2-cyanobiphenyl were added, followed by heating under reflux for 3 hours. After the reaction mixture was cooled, crystals so precipitated were collected by filtration, washed successively with ethanol and diethyl ether and then dried, whereby 2.54 g of the title compound was obtained.

(3) To 15 ml of isopropyl alcohol, 2.7 g of 2-amino-5-ethyl-1,3,4-thiadiazole and 1.3 g of 4'-bromomethyl-2-cyanobiphenyl were added, followed by heating under reflux for 3 hours. After the reaction mixture was cooled, crystals so precipitated were collected by filtration, washed successively with isopropyl alcohol and diethyl ether and then dried, whereby 2.53 g of the title compound was obtained.

(4) To a mixed solution of 7.5 ml of isopropyl alcohol and 2.5 ml of water, 2.7 g of 2-amino-5-ethyl-1,3,4-thiadiazole and 1.3 g of 4'-bromomethyl-2-cyanobiphenyl were added, followed by heating under reflux for 2 hours. After the reaction mixture was cooled, the crystals so precipitated were collected by filtration, washed successively with isopropyl alcohol and diethyl ether and then dried, whereby 2.11 g of the title compound was obtained.

(5) To 10 ml of acetonitrile, 2.7 g of 2-amino-5-ethyl-1,3,4-thiadiazole and 1.3 g of 4'-bromomethyl-2-cyanobiphenyl were added, followed by heating under reflux for 3 hours. After the reaction mixture was cooled, the crystals so precipitated were collected by filtration, washed successively with acetonitrile and diethyl ether and then dried, whereby 2.78 g of the title compound was obtained.

(6) To 10 ml of acetone, 2.7 g of 2-amino-5-ethyl-1,3,4-thiadiazole and 1.3 g of 4'-bromomethyl-2-cyanobiphenyl were added, followed by heating under reflux for 2 hours. After the reaction mixture was cooled, the crystals so precipitated were collected by filtration, washed successively with acetone and diethyl ether and then dried, whereby 2.14 g of the title compound was obtained.

(7) To 10 ml of chloroform, 2.7 g of 2-amino-5-ethyl-1,3,4-thiadiazole and 1.3 g of 4'-bromomethyl-2-cyanobiphenyl were added, followed by heating under reflux for 2 hours. After the reaction mixture was cooled, the crystals so precipitated were collected by filtration, washed successively with chloroform and diethyl ether and then dried, whereby 2.80 g of the title compound was obtained.

Example 3

Synthesis of 5-ethyl-2-imino-3-(2'-cyanobiphenyl-4-yl)methyl-1,3,4-thiadiazoline To a suspension of 4.0 g of 5-ethyl-2-imino-3-(2'-cyanobiphenyl-4-yl)methyl-1,3,4-thiadiazoline.hydrobromide in 60 ml of chloroform, 10 ml of 2N sodium hydroxide was added, followed by stirring at room temperature for one hour. After separation, the organic layer was dried over anhydrous magnesium sulfate, and then concentrated under reduced pressure. The resulting oil was crystallized from n-hexane, whereby 2.99 g of the title compound was obtained.

Melting point: 85–86° C.

$^1$H-NMR (CDCl$_3$): 1.24 (3H, t, J=7 Hz), 2.64 (2H, q, J=7 Hz), 5.13 (2H, s), 7.40–7.78 (8H, m).

Example 4

Synthesis of 5-ethyl-2-imino-3-[2'-(1H-tetrazol-5-yl)biphenyl-4-yl]methyl-1,3,4-thiadiazoline.hydrochloride To 1 liter of toluene, 490.8 g of 2-trifluoroacetylimino-5-ethyl-3-(2'-cyanobiphenyl-4-yl)methyl-1,3,4-thiadiazoline and 485.8 g of trimethyltin azide were added, followed by heating under reflux for 40 hours. To the reaction mixture, 200 ml of concentrated hydrochloric acid was added, and the resulting mixture was stirred for 10 minutes. The reaction mixture was then extracted with 5 liters of ethyl acetate. The organic layer was washed with water and dried over anhydrous magnesium sulfate. The solvent was removed under reduced pressure.

To the resulting residue, 4 liters of tetrahydrofuran, 200 ml of water and 94.4 g of sodium hydroxide were added, followed by heating under reflux for 7 hours. The reaction mixture was concentrated under reduced pressure. To the concentrate, water and ethyl acetate were added. To the aqueous layer so obtained, hydrochloric acid was added to make it acidic. The crystals so precipitated were collected by filtration, whereby 168 g of the title compound was obtained.

Appearance: Colorless powder

Melting point: 205–206° C.

$^1$H-NMR (DMSO-$d_6$): 1.22 (3H, t, J=8 Hz), 2.89 (2H, q, J=8 Hz), 5.43 (2H, s), 7.14 (2H, d, J=8 Hz) 7.28 (2H, d, J=8 Hz), 7.53–7.73 (4H, m).

Example 5

Synthesis of 5-ethyl-2-imino-3-[2'-(1H-tetrazol-5-yl)biphenyl-4-yl]methyl-1,3,4-thiadiazoline (1) In a 100-ml glass-made reactor equipped with a thermometer, a reflux condenser, a calcium chloride tube and a stirrer, 30 ml of n-butanol, 6.0 g of zinc chloride and 7.4 g of sodium azide were charged, and they were stirred for 30 minutes. In the reactor, 9.5 g of 5-ethyl-2-trifluoroacetylimino-3-(2'-cyanobiphenyl-4-yl)methyl-1,3,4-thiadiazoline were charged further, followed by heating. At the internal temperature of 105 to 115° C., the reaction was effected for 24 hours.

After confirming the disappearance of the raw materials by TLC, chloroform and water were added, each in an adequate amount. The resulting mixture was treated with 10% sulfuric acid, followed by separation. To the organic layer so obtained, a 5% aqueous solution of sodium hydroxide was added, followed by stirring for several hours. After confirming the hydrolysis by TLC, the reaction mixture was separated. The alkaline aqueous layer so obtained was neutralized with 3N hydrochloric acid. White crystals so precipitated were collected by filtration and dried, whereby 6.5 g of the title compound was obtained.

Melting point: 148–149° C.

$^1$H-NMR (DMSO-$d_6$): 1.15 (3H, t, J=7 Hz), 2.70 (2H, q, J=7 Hz), 5.10 (2H, s), 7.09 (2H, d, J=8 Hz), 7.18 (2H, d, J=8 Hz), 7.44–7.63 (4H, m).

(2) In 20 ml of toluene, 2.0 g of 5-ethyl-2-imino-3-(2'-cyanobiphenyl-4-yl)methyl-1,3,4-thiadiazoline.hydrobromide and 1.1 g of trimethyltin azide were suspended, followed by heating under reflux for 6 hours. After cooling, the reaction mixture was subjected to column chromatography on a silica gel and eluted using chloroform:methanol (20:1)→chloroform:methanol:acetic acid (20:10:1). The eluate fraction thus obtained were then distilled off under reduced pressure. To the residue, 40 ml of 2N sodium hydroxide and 40 ml of ethyl acetate were added. The aqueous layer so obtained was neutralized with 12N hydrochloric acid and powders so precipitated were collected by filtration. The powders were washed successively with water, ethanol and then diethyl ether and then dried, whereby 56 mg of the title compound was obtained.

(3) In 10 ml of toluene, 1.6 g of 5-ethyl-2-imino-3-(2'-cyanobiphenyl-4-yl)methyl-1,3,4-thiadiazoline and 1.1 g of trimethyltin azide were suspended, followed by heating under reflux for 4 hours. After cooling, the reaction mixture was subjected to column chromatography on a silica gel and eluted using chloroform:methanol (20:1) →chloroform:methanol:acetic acid (20:10:1). The eluate fractions thus obtained were distilled off under reduced pressure. To the resulting residue, 40 ml of 2N sodium hydroxide and 40 ml of ethyl acetate were added. The aqueous layer so obtained was neutralized with 12N hydrochloric acid and powders so precipitated were collected by filtration. The powders were successively washed with water, ethanol and diethyl ether and then dried, whereby 290 mg of the title compound was obtained.

(4) In a 500-ml glass-made reactor equipped with a thermometer and a reflux condenser, 200 ml of n-butanol, 37.5 g of zinc chloride and 50.7 g of sodium azide were charged, followed by stirring for 30 minutes. To the reactor, 50 g of 5-ethyl-2-imino-3-(2'-cyanobiphenyl-4-yl)methyl-1,3,4-thiadiazoline were charged further, followed by heating the internal temperature to 110 to 120° C. at which the reaction was effected for 20 hours. After the completion of the reaction, the reaction mixture was cooled. After the internal temperature decreased to 100° C. or lower, adequate amounts of chloroform and 10% sulfuric acid were added to the reaction mixture, followed by stirring for 30 to 60 minutes. The reaction mixture was cooled and then separated. To the organic layer, a 5% aqueous solution of sodium hydroxide was added. The resulting mixture was stirred for several hours, followed by separation into layers. The aqueous layer was adjusted to pH 7 with 3N hydrochloric acid. The white crystals so precipitated were collected by filtration. The crude crystals so obtained were washed with chloroform under heating and then cooled to room temperature. After cooling to room temperature, the reaction mixture was collected by filtration and dried, whereby about 44.8 g of the title compound was obtained.

Example 6

Synthesis of 2-[[5-ethyl-3-[2'-(1H-tetrazol-5-yl) biphenyl-4-yl]methyl-1,3,4-thiadiazolin-2-yliden] aminocarbonyl]-1-cylcopentenecarboxylic acid (1) To 2 ml of N,N-dimethylformamide, 200 mg of 5-ethyl-2-imino-3-[2'-(1H-tetrazol-5-yl)biphenyl-4-yl] methyl-1,3,4-thiadiazoline hydrochloride and 76 mg of 1-cyclopentene-1,2-dicarboxylic anhydride were added and the resulting mixture was stirred at room temperature for 2 hours. Water was added to the reaction mixture and the crystals so precipitated were collected by filtration. The crystals were washed with water and ethanol and then dried, whereby 170 mg of the title compound was obtained.

Appearance: Colorless crystals
Melting point: 234–235° C.

$^1$H-NMR (DMSO-d$_6$): 1.25 (3H, t, J=8 Hz), 1.83–1.94 (2H, m), 2.71–2.88 (4H, m), 2.92 (2H, q, J=8 Hz), 5.50 (2H, s), 7.09 (2H, d, J=8 Hz), 7.33 (2H, d, J=8 Hz), 7.53–7.70 (4H, m).

(2) In 30 ml of N,N-dimethylformamide, 3.63 g of 5-ethyl-2-imino-3-[[2'-(1H-tetrazol-5-yl)biphenyl-4-yl] methyl]-1,3,4-thiadiazoline was dissolved, followed by the addition of 1.44 g of 1-cyclopentene-1,2-dicarboxylic anhydride. The resulting mixture was stirred at room temperature for 6 hours. To the reaction mixture, 200 ml of water and 5 ml of hydrochloric acid were added. The powders so precipitated were collected by filtration. The powders so obtained were suspended in 100 ml of ethanol and the resulting suspension was heated under reflux for 20 minutes. The powders were collected by filtration, washed successively with ethanol and diethyl ether and then dried, whereby 4.53 g of the title compound was obtained.

Example 7

Synthesis of Dipotassium 2-[[5-ethyl-3-[2'-(1H-tetrazol-5-yl)biphenyl-4-yl]methyl-1,3,4-thiadiazolin-2-ylidene]aminocarbonyl]-1-cyclopentenecarboxylate In a mixed solution containing 15 ml of water and 16 ml of a 0.5N potassium hydroxide solution in ethanol, 2.0 g of 2-[[5-ethyl-3-[2'-(1H-tetrazol-5-yl)biphenyl-4-yl]methyl-1, 3,4-thiadiazolin-2-yliden]aminocarbonyl]-1-cyclopentenecarboxylic acid was dissolved. From the resulting solution, the solvent was distilled off. To the residue, 50 ml of ethanol was added, and the resulting mixture was allowed to stand overnight. The crystals so precipitated were collected by filtration and dried, whereby 2.24 g of the title compound was obtained.

Melting point: 300° C. or higher.
IR(KBr) cm$^{-1}$: 1642 (—COOK), 1570 (=N—CO—)
$^1$H-NMR (D$_2$O): 1.23 (3H, t, J=8 Hz), 1.95–2.00 (2H, m), 2.66–2.86 (6H, m), 5.49 (2H, s), 7.04 (2H, d, J=8 Hz), 7.31 (2H, d, J=8 Hz), 7.37–7.39 (1H, m), 7.51–7.62 (3H, m).

Example 8

Synthesis of Monopotassium 2-[[5-ethyl-3-[2'-(1H-tetrazol-5-yl)biphenyl-4-yl]methyl-1,3,4-thiadiazolin-2-yliden]aminocarbonyl]-1-cyclopentenecarboxylate To 206 mg of 2-[[5-ethyl-3-[2'-(1H-tetrazol-5-yl) biphenyl-4-yl]methyl-1,3,4-thiadiazolin-2-ylidene] aminocarbonyl]-1-cyclopentenecarboxylic acid, 8.3 ml of a 0.05N potassium hydroxide solution in ethanol and 50 ml of ethanol were added, followed by heating over water bath to dissolve completely. From the resulting solution, the solvent was distilled off under reduced pressure. To the residue, ethanol was added and the solid so precipitated was collected by filtration. The solid was dried under reduced pressure, whereby 180 mg of the title compound was obtained.

IR(KBr) cm$^{-1}$: 1680 (—COOH), 1570 (=N—CO—).

CAPABILITY OF EXPLOITATION IN INDUSTRY

According to the present invention, a tetrazolylated biphenylmethane derivative (6) or a salt thereof which is useful as a pharmaceutical can be industrially and advantageously prepared with short steps.

We claim:

1. A process for producing a tetrazolylated biphenyl-methane derivative represented by the following formula (6):

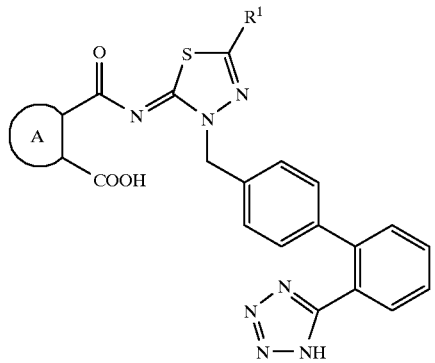

wherein $R^1$ represents a lower alkyl group, and ring A represents a cycloalkane, cycloalkene or benezene ring, which comprises reacting a 2-amino-1,3,4-thiadiazole represented by the following formula (1):

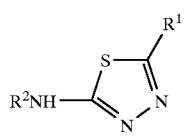

wherein $R^1$ has the same meaning as defined above and $R^2$ represents a hydrogen atom or an amino-protecting group with a cyanated biphenylmethane represented by the following formula (2):

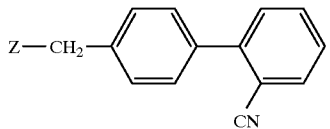

wherein Z represents a halogen atom or a sulfonyloxy group, reacting the resulting compound represented by the following formula (3):

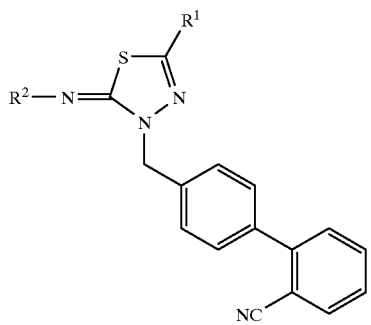

wherein $R^1$ and $R^2$ have the same meanings as defined above with a metal azide compound and an acid, eliminating the protecting group when there exists an amino-protecting group, and reacting the resulting compound represented by the following formula (4):

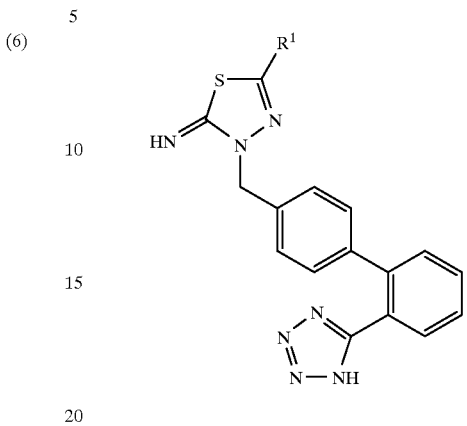

wherein $R^1$ has the same meaning as defined above with an acid anhydride represented by the following formula (5):

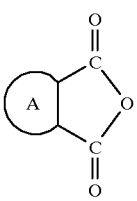

wherein ring A has the same meaning as defined above.

2. The process as claimed in claim 1, wherein the lower alkyl group represented by $R^1$ is a linear or branched alkyl group having 1 to 7 carbon atoms.

3. The process as claimed in claim 1, wherein the lower alkyl group represented by $R^1$ is selected from the group consisting of methyl, ethyl, n-propyl, isopropyl, n-butyl, t-butyl, and n-pentyl.

4. The process as claimed in claim 1, wherein the cycloalkane represented by the ring A is a cycloalkane having 3 to 7 carbon atoms.

5. The process as claimed in claim 1, wherein the cycloalkane represented by ring A is selected from the group consisting of cyclopropane, cyclobutane, cyclopentane, cyclohexane and cycloheptane.

6. The process as claimed in claim 1, wherein the cycloalkene represented by ring A is a cycloalkene having 3 to 7 carbon atoms.

7. The process as claimed in claim 1, wherein the cycloalkene represented by ring A is selected from the group consisting of cyclopropene, cyclobutene, cyclopentene, cyclohexene and cycloheptene.

8. The process as claimed in claim 1, wherein $R^2$ is a hydrogen atom.

9. The process as claimed in claim 1, wherein the amino-protecting group represented by $R^2$ is an acyl group.

10. The process as claimed in claim 1, wherein the amino-protecting group represented by $R^2$ is an acyl group selected from the group consisting of acetyl and trifluoroacetyl groups.

11. The process as claimed in claim 1, wherein the halogen atom represented by Z is selected from the group consisting of chlorine, bromine and iodine.

12. The process as claimed in claim 1, wherein the sulfonyloxy group represented by Z is selected from the group consisting of alkylsulfonyloxy and arylsulfonyloxy group.

13. The process as claimed in claim 1, wherein the metal azide compound is selected from the group consisting of tri($C_{1-18}$ alkyl) tin azide, tri($C_{1-18}$ alkyl)silyl azide and sodium azide.

14. The process as claimed in claim 1, wherein the acid is selected from the group consisting of mineral acids and Lewis acids.

15. The process as claimed in claim 1, further comprising converting the tetrazolylated biphenylmethane derivative represented by formula (6) into a pharmaceutically acceptable salt.

16. The process as claimed in claim 15, further comprising purifying the pharmaceutically acceptable salt of the tetrazolylated biphenylmethane derivative represented by the formula (6).

17. The process as claimed in claim 1, further comprising purifying the tetrazolylated biphenylmethane derivative represented by the formula (6).

\* \* \* \* \*